US009102893B2

(12) United States Patent
Custis et al.

(10) Patent No.: US 9,102,893 B2
(45) Date of Patent: Aug. 11, 2015

(54) EQUIPMENT LUBRICATING MICROBIAL COMPOSITIONS

(75) Inventors: Daniel B. Custis, Van Wert, OH (US); Martin C. Robinson, Cedar Rapids, IA (US)

(73) Assignee: Advanced Biological Marketing, Van Wert, OH (US)

( * ) Notice: Subject to any disclaimer, the term of this patent is extended or adjusted under 35 U.S.C. 154(b) by 1194 days.

(21) Appl. No.: 12/119,178

(22) Filed: May 12, 2008

(65) Prior Publication Data

US 2009/0048128 A1 Feb. 19, 2009

Related U.S. Application Data

(63) Continuation-in-part of application No. 11/517,051, filed on Sep. 7, 2006.

(60) Provisional application No. 60/715,076, filed on Sep. 8, 2005.

(51) Int. Cl.

| | |
|---|---|
| ***C10M 103/02*** | (2006.01) |
| ***C10M 111/06*** | (2006.01) |
| ***C10M 113/02*** | (2006.01) |
| *C12N 1/14* | (2006.01) |
| *C12N 1/20* | (2006.01) |

(52) U.S. Cl.

CPC ........... *C10M 111/06* (2013.01); *C10M 113/02* (2013.01); *C10M 2201/0413* (2013.01); *C10M 2201/10* (2013.01); *C10M 2201/1033* (2013.01); *C10N 2250/16* (2013.01); *C12N 1/14* (2013.01); *C12N 1/20* (2013.01)

(58) Field of Classification Search

None

See application file for complete search history.

(56) References Cited

U.S. PATENT DOCUMENTS

| | | | | |
|---|---|---|---|---|
| 4,670,248 | A * | 6/1987 | Schricker | 424/438 |
| 4,711,656 | A | 12/1987 | Kaneshiro | |
| 5,041,383 | A | 8/1991 | Paau et al. | |
| 5,188,634 | A | 2/1993 | Hussein | |
| 5,215,747 | A | 6/1993 | Hairston et al. | |
| 5,300,127 | A | 4/1994 | Williams | |
| 5,503,651 | A | 4/1996 | Kloepper et al. | |
| 5,503,652 | A | 4/1996 | Kloepper et al. | |
| 5,695,541 | A | 12/1997 | Kosanke et al. | |
| 5,697,186 | A | 12/1997 | Neyra et al. | |
| 5,798,252 | A | 8/1998 | Hobson et al. | |
| 5,849,320 | A * | 12/1998 | Turnblad et al. | 424/410 |
| 5,888,947 | A | 3/1999 | Lambert et al. | |
| 6,209,259 | B1 | 4/2001 | Madigan et al. | |
| 6,606,822 | B2 | 8/2003 | Bonfiglio | |
| 6,841,515 | B2 | 1/2005 | Burnham | |
| 6,900,162 | B2 | 5/2005 | Wertz et al. | |
| 6,951,075 | B2 | 10/2005 | Babler et al. | |
| 7,157,254 | B1 | 1/2007 | Akimoto et al. | |
| 7,213,367 | B2 | 5/2007 | Wertz et al. | |
| 2003/0068303 | A1 | 4/2003 | Selvig et al. | |
| 2004/0175389 | A1 | 9/2004 | Porubcan | |
| 2004/0220056 | A1 | 11/2004 | Glenn et al. | |
| 2005/0079342 | A1 | 4/2005 | Ye | |
| 2006/0029576 | A1 | 2/2006 | Huang et al. | |
| 2006/0240983 | A1 | 10/2006 | Yamaguchi | |
| 2007/0243235 | A1 | 10/2007 | David | |
| 2009/0093365 | A1 | 4/2009 | Walsh et al. | |

FOREIGN PATENT DOCUMENTS

| | | |
|---|---|---|
| CN | 1276973 | 12/2000 |
| EP | 0286351 | 10/1988 |
| EP | 0594125 | 4/1994 |
| EP | 603989 | 6/1994 |
| JP | 2001518121 A | 9/2001 |
| WO | WO9419924 | 9/1994 |
| WO | WO9604221 | 2/1996 |
| WO | WO03000051 A2 | 1/2003 |
| WO | WO03020837 | 3/2003 |
| WO | WO2004005219 | 1/2004 |
| WO | WO2005030383 | 4/2005 |
| WO | WO2007030557 | 3/2007 |

OTHER PUBLICATIONS

Jin, Xixuan and Custis, Daniel "Microencapsulating Aerial Conidia of Trichoderma harzianum Through Spray Drying at Elevated Temperatures" Biological Control, 56(2), Feb. 2011 (online Nov. 14, 2010), pp. 202-208, doi:10.1016/j.biocontrol.2010.11.008.*

Cole-Parmer "Cole-Parmer's FoodTechSource: Water Activity", Cole-Parmer Instrument Company, 2002, retreived from interent<http://www.foodtechsource.com/rcenter/tech_data/td_water.htm>, 3 pages (HTML text).

Garrity, G.M., Kuykendall, L.D., et al "Class1, Order VI, Family VII. Bradyrhizobiaceae fam. nov.: Genus I. Bradyrhizobium" Bergery's Manual of Systemativc Bacteriology, 2nd ed. 2005, vol. 2, chapter 32, pp. 438-443.

Schisler et al., "Formulation of Bacillus spp. for Biological Control of Plant Diseases," Phytopathology 94:1267-1271 (2004).

Zohar-Perez C et al: "Mutual relationships between soils and biological carrier systems" Biotechnology and Bioengineering, vol. 92, No. 1, Oct. 2005, pp. 54-60, XP002550257, ISSN: 0006-3592.

Pedreschi F et al, "Viability of dry Trichoderma harzianum spores under storage" Bioprocess Engineering, vol. 17, No. 3, 1997, pp. 177-183, XP002550258, ISSN: 0178-515X.

* cited by examiner

*Primary Examiner* — Rosanne Kosson
*Assistant Examiner* — Aaron J Kosar
(74) *Attorney, Agent, or Firm* — Standley Law Group LLP

(57) ABSTRACT

An exemplary embodiment is directed to an equipment lubricating composition comprising useful microorganisms. An exemplary embodiment comprises a water insoluble, water-absorbent substance and an encapsulated microorganism component including viable microorganisms. This encapsulating material may encapsulate and protect the microorganisms by essentially preventing the microorganisms from contacting the external environment. Based on the protection afforded by the encapsulation, exemplary embodiments may include previously inhospitable carrier compounds such as particulate machine lubricants.

11 Claims, No Drawings

EQUIPMENT LUBRICATING MICROBIAL COMPOSITIONS

CROSS-REFERENCE TO RELATED APPLICATIONS

This application claims priority to U.S. patent application Ser. No. 11/517,051 filed Sep. 7, 2006, which claims the benefit of U.S. Provisional Application Ser. No. 60/715,076 filed Sep. 8, 2005. All of the referenced applications, along with International Application No. PCT/US2006/034744, are hereby expressly incorporated by reference in their entirety.

TECHNICAL FIELD

The disclosed embodiments relate to formulations of viable microorganisms for industrial and agricultural applications.

BACKGROUND

Certain microorganisms are produced in large quantities and can be formulated for various commercial uses. For example, microbial products have been used in agriculture to protect plants from pests and diseases, to improve plant performance and nutrition, and as inoculants for silages. These microbial products must be produced in a way that is efficient, free of contamination, and suitable for maintaining high levels of viable microorganisms. Production of microbial formulations for commercial use requires drying the microorganisms in a way that preserves viability of the microbes, provides a suitable medium for commercial use, and maintains an extended shelf life of the microbial product.

A range of microorganisms have been produced and formulated for commercial use. Examples of commercially formulated microorganisms include strains of *Lactobacillus* spp. for a variety of food, probiotic, and animal feed uses; entomophagous fungi, such as *Beaveria* and *Metarhizum* spp., for control of plant-attacking insects; fungi that protect plants from diseases, such as *Trichoderma* and *Clonostachys* spp.; bacteria that protect plants from disease, such as *Pseudomonas* and *Bacillus* spp., as well as *Rhizobium* and *Bradyrhizobium*; and related bacteria that fix nitrogen through a symbiotic relationship with legumes and fungi, such as *Colletotrichum* spp., which are used as weed controls by causing disease in weeds.

Peat-based inoculants presently constitute the vast majority of inoculants marketed today, and their development is primarily due to their convenience in holding and distributing desired microorganisms. In the known art, such soil-like compositions are required in order to provide a substrate and a food source for the microorganisms in the interim period before the microbial products are applied to such materials as seed or plants. For example, in order to maintain high levels of viable microorganisms, useful microbial products relating to inoculants such as *Rhizobium* have typically been packaged in a peat medium or other humus-type carrier.

Many times peat requires processing before it may serve as a carrier medium for desired microorganisms. For example, at least one U.S. patent describes a typical process in which pH adjusted sedge peat is oven dried and milled in a hammer mill before being passed through a sieve. The powdered peat is sealed into polyethene bags and sterilized by gamma radiation. All of this occurs before sterilized packs are then injected with the desired microorganisms. Post injection, the injection hole is then re-sealed to prevent contamination.

The use of peat or other humus-type materials is problematic as a carrier medium. First, peat and many other humus-type carrier materials in the known art are abrasive. Planting equipment and many other types of equipment may be sensitive to the added friction introduced by the presence of peat in the formulation. Therefore, when peat based inoculants are applied to the seed, these formulations may actually increase the friction in the planting equipment (or other industrial equipment which may be used). Peat-based inoculants may tend to increase seed binding and bridging in planter hoppers, and additionally, may increase the wear and tear on critical metering parts and equipment.

Although humus-type materials can sustain desired microbes for extended periods, these compositions may be equally suitable for promoting the growth of contaminate species. These species may negatively affect the performance of the desired microorganisms. Although sterilizing the peat may provide a contaminate-free starting point, contaminate species may ultimately infiltrate and affect the performance of the inoculants.

Accordingly, new and improved methods of producing microbial products that are machine friendly, resistant to contaminate microorganisms, and which continue to have high activity levels and an extended shelf life are needed. Exemplary embodiments are directed to overcoming these and other limitations in the art.

SUMMARY

This and other unmet needs of the prior art are met by embodied compositions and methods as described in more detail below. An exemplary embodiment disclosed herein is directed to an equipment lubricating composition comprising useful microorganisms. An exemplary embodiment comprises a water insoluble, water-absorbent substance and an encapsulated microorganism component including viable microorganisms. This encapsulating material may encapsulate and protect the microorganisms by essentially preventing the microorganisms from contacting the external environment. Based on the protection afforded by the encapsulation, exemplary embodiments may include previously inhospitable carrier compounds such as particulate machine lubricants.

In a preferred embodiment, the microorganisms (or propagules) will be present in sufficient numbers and with sufficient activity to be effective for a particular agricultural or industrial application. Preferably, the microorganisms may be present in the formulation in an amount of at least about $5\times10^8$ colony forming units ("cfu") per gram of formulation. Finally, an exemplary embodiment may comprise a machine lubricant carrier component. In a preferred embodiment the lubricant comprises at least one of talc and graphite. For example, machine lubricants such as talc and/or graphite may comprise between about 5-95% of the entire equipment lubricating composition.

Exemplary embodiments also relate to a method of producing equipment lubricating compositions. An exemplary embodiment may include the steps of providing an aqueous suspension of viable microorganisms; contacting the aqueous suspension with an encapsulating material wherein said encapsulating material is capable of encapsulating the microorganisms; combining the aqueous suspension with a water insoluble, water-absorbent substance under conditions effective to produce a formulation of viable encapsulated microorganisms; and combining the encapsulated microorganisms with a particulate machine lubricant. In a preferred method, the particulate machine lubricant may comprise talc and or graphite.

An exemplary embodiment relates to a method for providing agriculturally useful microorganisms in a lubricating carrier substrate in a stable product form. For example. exemplary embodiments may be stable for packaging and shelving for extended periods at normal ambient temperatures. Furthermore, because exemplary embodiments have low water activities, they are resistant to contaminating microorganisms.

At least one exemplary embodiment relates to method of treating a plant or a plant seed with an equipment lubricating composition. This method involves providing the equipment lubricating composition as described supra and applying the preparation or the formulation to a plant or plant seeds under conditions effective to treat the plant or plant seed. Because these compositions comprise helpful lubricants, they will mitigate the friction caused by processing the microbial products and the materials contacted by those products in agricultural or industrial equipment such as, for example, planting equipment.

An exemplary embodiment describes a simple process of drying and formulating fungal and bacterial microorganisms that is inexpensive, requires little equipment, and provides products with excellent viability. An exemplary embodiment is free of peat or abrasive materials that contribute to the friction of processing the microbial product. Furthermore, because the example compositions may be co-formulated with a machine lubricant medium, they may actually mitigate the friction caused by processing the materials that may be contacted by the microbial products.

The formulations of exemplary embodiments possess sufficient activity of the microorganism to be effective in a variety of applications, including applications that require suspension in water, such as spray, drip irrigation, and other water-based deliver system applications. The formulations of the exemplary embodiments are non-dusty and have a high level of cosmetic appeal. The shelf life of the formulations of an exemplary embodiment is significantly longer than the shelf life of current formulations.

Formulations of an exemplary embodiment may also protect desired microorganisms from the toxic effects of other biological agents or chemicals (e.g., pesticides), providing the opportunity to produce co-formulations of these materials. In addition, the formulations of an exemplary embodiment comprise a barrier to prevent growth of undesirable microorganisms which increases the biological efficacy of the desired microorganism. The method of an exemplary embodiment reduces the amount of downstream processing and, therefore, minimizes the amount of damage that delicate microbial cells or spores may sustain.

DESCRIPTION

U.S. patent application Ser. No. 11/517,051, fully incorporated by reference in its entirety, discloses formulations for microorganisms. That application also discloses methods for producing and utilizing those formulations. Exemplary embodiments described herein utilize the microbial products and methods described in application Ser. No. 11/517,051, particularly those directed toward encapsulated microorganisms, along with other substances to produce new and useful compositions and methods. Exemplary embodiments described herein are directed at new and useful compositions made possible because of the protection afforded by encapsulating desired microorganisms.

An exemplary embodiment includes an equipment lubricating composition including a water insoluble, water-absorbent substance and an encapsulated microorganism component. The encapsulated microorganism component may include an effective amount of viable microorganisms and an encapsulating material which is capable of encapsulating the microorganisms under appropriate conditions. Remarkably, exemplary embodiments may also be co-formulated with significant quantities of machine lubricants. For example, the equipment lubricating compositions may include a particulate machine lubricant such as talc and or graphite. In an exemplary embodiment, the particulate machine component may comprise about 5-95% of the weight of the final composition. Furthermore, exemplary embodiments do not require the presence of peat or other soil-like adjuvant.

Even with the presence of significant amounts of machine lubricant, the encapsulated microorganism component of an exemplary embodiment may comprise an effective amount of viable microorganisms to inoculate a target material (e.g., seed, plant, or other material capable of being inoculated). The effective amount of viable microorganisms necessary to inoculate a given target material may vary considerably depending on the desired microorganism and the intended application. For some applications, an effective amount of viable microorganisms will be at least about $5\times10^6$ cfu per gram of the formulation. In other applications, an effective amount will be at least about $5\times10^8$ cfu per gram of the formulation.

Specific exemplary embodiments relate to a method of producing equipment lubricating compositions. An exemplary embodiment may include the steps of providing an aqueous suspension of viable microorganisms; contacting the aqueous suspension with an encapsulating material wherein said encapsulating material is capable of encapsulating the microorganisms; combining the aqueous suspension with a water insoluble, water-absorbent substance under conditions effective to produce a formulation of viable encapsulated microorganisms; and combining the encapsulated microorganisms with a particulate machine lubricant. In a preferred method, the particulate machine lubricant may comprise talc and or graphite.

Combining the aqueous suspension of viable microorganisms with the water insoluble, water-absorbent substance can be carried out by a variety of methods. In a preferred embodiment, the combining step is carried out by kneading the aqueous suspension with the water insoluble, water absorbent substance.

Exemplary methods may use viable microorganisms provided in an aqueous suspension, or an otherwise suitable environment for maintaining the viability of the microorganisms. The aqueous suspension of viable microorganisms may then be contacted with an encapsulating material. When the aqueous suspension of viable microorganisms containing an encapsulating material is combined with a water insoluble, water-absorbent substance, the viable microorganisms may be encapsulated. Preferably, the encapsulation may occur as the water insoluble, water-absorbent substance absorbs water from the suspension containing the encapsulating material. As the water insoluble, water absorbent substance begins to sequester the fluid, the encapsulating material may form microbeads or capsules which may provide a relative zone of protection for the microorganisms so encapsulated.

In an exemplary embodiment, the water insoluble, water-absorbent substance can be any organic or inorganic material capable of removing moisture gently from the suspension of viable microorganisms. Suitable inorganic substances include zeolite, porous beads or powders, silica, and the like.

Suitable organic substances include plant materials, such as ground agricultural products (e.g., corn cobs), porous wood products, cellulose, and the like. In addition, cyclodextrins may be useful as water insoluble, water-absorbent substances. Cyclodextrins are widely used in many industries for encapsulation/binding of a wide variety of relatively apolar materials.

Cyclodextrins are inexpensive, available in bulk quantities, and have low solubility in water (depending upon the actual composition of the cyclodextrin molecule). Cyclodextrins can be used as formulating agents to sequester liquid or apolar solid materials that can be suspended in water, such as pesticides and pesticide adjuvant. Any combination of the above-described water insoluble, water-absorbent substances may also be used. In a preferred embodiment, the water insoluble, water-absorbent substance is a finely ground cellulose powder.

The water insoluble, water-absorbent substance is combined with the aqueous suspension of viable microorganisms to an amount of about 80 to 99% by total weight of the pre-lubricant formulation. Thus, the aqueous suspension of viable microorganism is present in the formulation in an amount of about 1 to 20% by total weight of the formulation. Preferably, the water insoluble, water-absorbent substance is present in the formulation in the amount of at least about 80%, 85%, 90%, 95%, or 99% by total weight of the pre-lubricant formulation.

In an exemplary embodiment, the encapsulating material is a water soluble material capable of forming a film or microbead when dried. Suitable encapsulating materials include, without limitation, native or modified chitosans, native or modified starches, glucans or dextrins, celluloses modified so they are soluble, and any of a number of native or modified vegetable or microbial gums, including agars, guar, locust, carrageenan, xanthans, pectins, and the like, and combinations thereof. In at least one exemplary embodiment, the encapsulating material is a dextrin, such as that commercially available under the registered trademark CRYSTAL-TEX from National Starch and Chemical Co., Bridgewater, N.J.

Encapsulating the microorganisms provides many advantages. In particular, due to the protection afforded by encapsulation, an exemplary embodiment may comprise a machine lubricant carrier component. In a preferred embodiment the lubricant may comprises at least one of talc and graphite. For example, machine lubricants such as talc and/or graphite may comprise between about 5-95% of the entire equipment lubricating composition.

Machine lubricating powders such as talc and graphite are normally inhospitable to most microorganisms. However, because the encapsulated microorganisms are essentially isolated from external contact, the encapsulated microorganisms may be co-formulated with essentially dry machine lubricants such as talc and graphite. Various other particulate machine lubricants may also be used with acceptable results. For example, granulated polytetrafluoroethylene, commercially available under the registered trademark TEFLON or other materials with similar properties may be appropriate for particular applications.

Encapsulated microorganisms may be more resistant to chemical pesticides, which may dramatically reduce the shelf life of non-encapsulated microorganisms by contact toxicity. For example, it may be desirable to combine encapsulated microorganisms with other chemical or biological agents. When the microorganisms are placed together in a container with e.g., a chemical fungicide, the chemical fungicide would be detrimental to a non-encapsulated microorganism. Thus, encapsulation prevents contact of the microorganisms with the chemical pesticide, unless the chemical pesticide has a significant vapor pressure. Encapsulation of the microorganisms may, therefore, be advantageous when formulating mixtures of microorganisms with chemical pesticides and other biological products.

In exemplary embodiments, encapsulation provides an opportunity to define a targeted environment for the desired microorganisms. The microbeads or capsules that encapsulate the useful microorganisms can be manipulated to increase the survival and activity of the microorganisms they encapsulate. For example, nutritional supplements that favor the desired microorganism may be added to the pre-encapsulation suspension. In some embodiments, the encapsulation material itself may be selected to provide a food source for the encapsulated microorganisms.

Exemplary embodiments disclosed herein may not only eliminate the requirement for peat or other peat-like materials, they also contain lubricants designed to lubricate the machinery and equipment which may be used to process the desired seeds or plants. Based on the protective properties afforded by the microbeads that encapsulate the desired microorganisms, the target microorganisms may be packaged with normally inhospitable compounds. Furthermore, the encapsulated microorganisms do not require peat or any other material to sustain the activity or survival of the microorganisms.

Proper lubrication is an important aspect of essentially all known machines. However, many microorganisms useful for industrial and agricultural purposes cannot survive for extended periods in the presence of dry machine lubricants such as talc and or graphite. First, the lubricants, such as talc or graphite, are not a food source for the microorganisms. Accordingly, if packaged without peat or similar life sustaining materials, most microorganisms will simply run out of food. Second, dry machine lubricants do not retain moisture. Therefore, the microorganisms will desiccate before they can be used in the relevant application. Therefore, the known art has been unable to package many useful microorganisms in a lubricant carrier without including significant amounts of a carrier compound such as peat.

Equipment lubricating compositions of viable microorganisms produced by the methods of the exemplary embodiments may be dried. However, drying of the microorganisms is preferably performed using methods that maintain the viability of the microorganisms. Drying may be performed before or after the machine lubricant is combined with the rest of the composition. In a preferred embodiment, the drying method is air drying. Air drying is a method that prevents the microorganisms from coming into contact with high temperatures. Drying the compositions may increase the shelf-life of exemplary embodiments.

The encapsulated microorganism component of exemplary embodiments may be dissolved when appropriate. Accordingly, a further aspect of an exemplary embodiment relates to a preparation of viable microorganisms including dissolving the soluble components of a disclosed embodiment in solution. The encapsulated microorganism component of exemplary embodiments may be suspended in a solution for commercial applications in a spray, drip irrigation, or other water-based delivery system.

However, this list of equipment and processes that may benefit from exemplary embodiments is not intended to be limiting. With appropriate measures well known to those of skill in the art, products and methods described herein may be used with many other mechanical delivery systems. Exemplary embodiments may be designed according to the scale and needs of a particular application.

Another aspect of an exemplary embodiment relates to method of treating a plant or a plant seed with an equipment lubricating composition containing desired microorganisms. This method involves providing a preparation or a formulation as described supra and applying the preparation or the formulation to a plant or plant seed under conditions and in an amount effective to treat the plant or plant seed. Because an exemplary embodiment includes a particulate machine lubricant, the application of the preparation to the plant or plant seeds may reduce the friction associated with processing the desired microorganisms themselves or the treated plant or plant seed. In an exemplary embodiment, the particulate machine lubricant will not dissolve and will be dispersed on the plant or plant seed.

Treating a plant or a plant seed according to the method of an exemplary embodiment may include, without limitation, imparting disease resistance, imparting resistance to pests, improving nutrition and/or yield, or any combination thereof.

In addition to the microorganisms themselves, propagules of the microorganisms may also be formulated pursuant to the methods of an exemplary embodiment. Propagules include, without limitation, fungal spores, hyphae, vesicles, and auxiliary cells. The microorganisms may have a commercial utility in agricultural applications and may be useful to control insect pests, weeds, and plant disease, or to provide nourishment to plants so that their growth and/or yield is increased. Suitable species of microorganisms include, without limitation, species of the genera *Bacillus* and *Pseudomonas* (useful for insect control); *Beauveria, Metarhizum*, and species of the division *Oomycota* (weed control); *Colletotrichum, Phytophthora, Trichoderma, Clonostachys*, and binucleate *Rhizoctonia* (to control plant diseases); and *Bradyrhizobium, Rhizobium* and related genera (to improve plant nutrition and yield including). Other similar microorganisms can also be formulated using the method of an exemplary embodiment. Microorganisms with commercial utility in food processing, brewing, and silage and sewage treatment are also suitable for formulation pursuant to the method of an exemplary embodiment. Preferred microorganisms may include species of the fungus *Trichoderma* and species of the bacteria *Bradyrhizobium.*

These and other aspects of the exemplary embodiments are further illustrated by the examples below.

EXAMPLES

Example 1

Preparation of Equipment Lubricating Compositions

To prepare the encapsulated microorganism component, a frozen paste of concentrate *Bradyrhizobium* from a commercial source was used as a starting material. The initial *Bradyrhizobium* suspension contained about 1 $\times 10^{12}$ colony forming units/ml of the bacterium. CRYSTAL TEX dextrin was added to the suspension to give a 4% w/v mixture and mixed until it was dissolved. Cellulose (commercially available under the registered trademark SIGMACELL TYPE 50 from Sigma Chemical Co., St. Louis, Mo.) was added to each preparation to give two volumes of cellulose for each volume of cell suspension +CRYSTAL TEX. These were mixed by kneading by hand in a plastic bag until a uniform mixture was obtained. The result was a free-flowing powder. This material was air dried until the water activity was approximately 0.55. This material constitutes an example encapsulated microorganism component.

A particulate machine lubricant comprising 18.8 ounces of talc and 4.7 ounces of graphite was combined with 1.5 ounces of the encapsulated microorganism component above. The package size of the finished product was 25 ounces.

Example 2

Characterization of the Product Composition

Sterile PBS was added to the preparation from Example 1 to dissolve the encapsulated microorganism component. A standard dilution plating protocol was performed to determine the cfu levels and stability of the graphite, talc, and encapsulated microorganisms in a finished formulation. The cfu counts of *Bradyrhizobia* in the final composition were determined to be $4\times10^9$ cfu/g.

The description of the disclosed embodiments is presented for purposes of clarity of understanding only, and no unnecessary limitations should be implied. It will be appreciated by those skilled in the art that embodiments may be practiced in various alternate forms and configurations. For example, although many of the examples discussed are directed to microorganisms useful in an agricultural context, it should be appreciated that the invention is not so limited. The concept exemplified in the example embodiments may apply broadly to other situations in which desired microbial products or the materials they treat may contact or be processed by machinery. Likewise, despite the fact that particular microorganisms are discussed in more detail than others, many other useful microorganisms which are not specifically mentioned may also be encapsulated and formulated pursuant to the compositions and methods exemplified by the disclosed embodiments. Microorganisms may include, without limitation, species from the kingdoms Eubacteria, Archaebacteria, Protista, and Fungi.

What is claimed is:

1. A microorganism-containing lubricating composition, comprising:

(a) microorganism component, encapsulated as microbeads by a water-soluble encapsulating material;

(b) a water insoluble, water-absorbent substance, present in an amount sufficient to maintain the composition as a dry, free-flowing powder; and (c) a particulate lubricant including at least one of talc and graphite.

2. The composition of claim 1, wherein the lubricating composition, by weight thereof, comprises the particulate lubricant in an amount of 5-95% (w/w).

3. The composition according to claim 2, wherein the water insoluble, water-absorbent substance is selected from the group consisting of zeolite, porous beads or powders, silica, ground agricultural products, porous wood products, cellulose, cyclodextrins, and combinations thereof.

4. The composition according to claim 2, wherein the water insoluble, water-absorbent substance is cellulose powder.

5. The composition according to claim 2, wherein the microorganisms of the microorganism component are selected from the group consisting of fungi, bacteria, and combinations thereof.

6. The composition according to claim 5, wherein the microorganisms are fungi.

7. The composition according to claim 6, wherein the fungi comprise a species from the genus *Trichoderma.*

8. The composition according to claim 5, wherein the microorganisms are bacteria.

9. The composition according to claim 8, wherein the bacteria comprise a species from the genus *Bradyrhizobium.*

10. A lubricating inoculant composition, comprising:

(a) a water insoluble, water-absorbent cellulose powder;

(b) a microorganism component, encapsulated in micro-beads of a water-soluble encapsulating material, the microorganism component providing an effective amount of viable microorganisms to inoculate a plant or plant seed; and (c) a particulate lubricant, comprising at least one of: talc and graphite.

11. The composition of claim 10, wherein: the water soluble encapsulating material is a dextrin.

* * * * *